United States Patent
Tatarek et al.

(10) Patent No.: US 6,568,391 B1
(45) Date of Patent: May 27, 2003

(54) OXYGEN THERAPY APPARATUS

(75) Inventors: Andrew Richard Thomas Tatarek, Hampshire (GB); Jonathan Mark St. John Harris, Worcestershire (GB)

(73) Assignee: Protector Technologies, B.V., Schiedam (NL)

( * ) Notice: Subject to any disclaimer, the term of this patent is extended or adjusted under 35 U.S.C. 154(b) by 0 days.

(21) Appl. No.: 09/530,283

(22) PCT Filed: Nov. 3, 1998

(86) PCT No.: PCT/GB98/03270

§ 371 (c)(1),
(2), (4) Date: Jun. 28, 2000

(87) PCT Pub. No.: WO99/22795

PCT Pub. Date: May 14, 1999

(30) Foreign Application Priority Data

Nov. 4, 1997 (GB) ............................................. 9723319

(51) Int. Cl.[7] ............................................. A61M 16/00
(52) U.S. Cl. ............................. 128/204.26; 128/204.23; 128/205.24
(58) Field of Search ....................... 128/204.26, 205.24, 128/204.18, 204.21, 204.23, 202.22, 203.14; 137/908

(56) References Cited

U.S. PATENT DOCUMENTS

| 3,434,471 | A | | 3/1969 | Liston ..................... 128/145.8 |
|---|---|---|---|---|
| 3,783,891 | A | * | 1/1974 | Christianson ................ 137/491 |
| 3,805,780 | A | * | 4/1974 | Cramer et al. ........... 128/142.2 |
| 4,054,133 | A | | 10/1977 | Myers ..................... 128/142.2 |
| 4,575,042 | A | | 3/1986 | Grimland et al. ............. 251/46 |
| 4,932,402 | A | * | 6/1990 | Snook et al. .......... 128/204.23 |
| 5,360,000 | A | | 11/1994 | Carter .................... 128/204.26 |
| 5,666,945 | A | * | 9/1997 | Davenport ............. 128/200.14 |
| 5,881,725 | A | * | 3/1999 | Hoffman et al. ....... 128/204.26 |

FOREIGN PATENT DOCUMENTS

| WO | 8702590 | 5/1987 | .......... A61M/16/00 |
|---|---|---|---|
| WO | 9640336 | 12/1996 | .......... A61M/16/00 |

* cited by examiner

*Primary Examiner*—Weilun Lo
*Assistant Examiner*—Mital Patel
(74) *Attorney, Agent, or Firm*—Volpe and Koenig, P.C.

(57) ABSTRACT

An oxygen therapy apparatus for supply of oxygen to patients. The device comprises an inlet port (17) for receiving high pressure oxygen from a cylinder and an outlet port (1) for supplying oxygen to a patient, typically via a single tube cannula (not shown). Three valves control the supply of oxygen to the patient: a diaphragm valve (42) senses the pressure at the outlet (1) and, in particular senses whether the patient is inhaling or exhaling. A valve (36) controls the supply of oxygen to the patient via an inlet jet (25) which is selectably closed by a piston (20) incorporating a flexible seat (24). Movement of the piston (20) is in turn controlled by a pilot valve (37) in dependence on the state of the diaphragm valve (42). The device gives a pulsed output to the patient during inhalation, but shuts off during exhalation to economise on the use of oxygen.

20 Claims, 4 Drawing Sheets

OXYGEN THERAPY APPARATUS

This invention relates to oxygen therapy apparatus for supply of breathable gas, for example, oxygen to patients.

Oxygen therapy is widely used in medical applications and is very widely applied in hospitals, with oxygen therapy capability to most hospital beds. However, many known oxygen therapy flow devices waste up to ⅔ of the oxygen delivered by the device due to the fact that the device delivers flow during the period when the patient is exhaling. There is further wastage, as only the oxygen delivered at the start of a breath goes deep into the lungs where it is absorbed. Furthermore, the patient's need and the available settings are often poorly matched; for example a person needing 2.5 L/m might have to have 4 L/m, because of the small number of settings available. The invention thus relates in particular to an oxygen economiser device for oxygen therapy apparatus which device seeks to reduce this wastage of oxygen.

Many patients are dependent on oxygen for mobility, and so have to carry cylinders lasting typically a couple of hours. An oxygen economiser device can be used to make the same cylinder last longer, or make a much smaller and lighter cylinder meet the existing time.

There are a number of oxygen economiser devices on the market, working by one of two ways. A first is an electrically operated device which builds up a reservoir of gas during exhalation and, as the patient starts to inhale, opens a valve for a moment, giving a pulse of oxygen into the first part of the inhaled breath. Variation in delivery is given by operating the unit every other breath, every third breath or every fourth breath. This saves the oxygen, but has a limited number of settings, and needs batteries and associated circuitry. Additionally such units normally have additional controls which are undesirable for the people using oxygen therapy.

A second device is one which incorporates what is effectively a demand valve with a diaphragm to detect the decrease in pressure on inhalation which (by pilot operation, say) opens a valve for the main flow, and closes it when exhalation ceases. This type of device has to have a twin tube supplying the patient, since the resistance of the tube during flow (say 500 mm $H_2O$) is many times the magnitude of the signal, so is too great to allow the slight negative pressure signal (say 3 mm $H_2O$) to the diaphragm, so would close the diaphragm.

According to the invention there is provided a pneumatically operated economiser device for supply of breathable gas to a patient, said device having an inlet port for receiving a supply of pressurised gas and an outlet port for delivering a supply of pressurised gas to the patient, valve means between the inlet port and the outlet port, said valve means being switchable between a first position in which flow of gas from the inlet port to the outlet port is prevented, and a second position in which gas may flow from said inlet port to said outlet port, means for monitoring for inhalation by the patient, actuator means normally maintaining the valve means in said first position but switching said valve means to said second position when the pressure at the outlet port, as detected by said monitoring means, falls below a preset level indicative of inhalation, and delay means for maintaining the valve means in said second position for a preset period.

Generally speaking, the breathable gas will be oxygen and, for convenience, this will be assumed throughout the following description. However gases other than oxygen, and mixtures of oxygen with other gases or vapours are possible.

Preferably said preset period is less than the expected period of inhalation and advantageously it is considerably shorter than the inhalation period. A typical preset period is about 0.5 seconds.

The monitoring means is preferably operable to continuously monitor the outlet pressure during exhalation, and to sample it at regular spaced intervals sufficiently small not to cause delay in the switching of the valve means to the open position during inhalation.

At the end of the preset delay period, the valve means reverts to the closed condition but if, at this point, the monitoring means is still indicating that inhalation is taking place, the actuator means will immediately re-open the valve to allow the supply of oxygen to recommence. This opening and closing of the valve means will continue until such time as, at the end of a preset delay period, the monitoring means indicates that exhalation has commenced. During exhalation, the valve means remains in said first position— i.e. closed.

Thus, during inhalation, the patient receives a pulsed flow of oxygen having a period equal to the aforementioned preset period. During exhalation no oxygen is supplied, thus resulting in a significant saving of oxygen over conventional oxygen therapy devices which do not use oxygen economiser techniques.

This invention allows the use of single tube cannulas and single tube is face masks, as used in conventional (non oxygen economiser) oxygen therapy devices. Known oxygen economiser devices make use of two tubes leading to the patient, one to supply the oxygen, and one to monitor the status of the breathing cycle. The device of the invention is thus able to utilise existing (single tube) cannulas which are more comfortable for the patient, and do not result in supply being tied to a particular manufacturer.

In the present invention the outlet port is two way, and therefore both transmits the outgoing oxygen to the patient, and receives a pressure signal resulting from the exhaled breath from the patient. The monitor is operable to monitor the pressure at the outlet port and thus inevitably monitors both the pressure of oxygen during inhalation and the pressure of exhalation. Four conditions at the outlet port can be identified:

1) The valve means is closed and exhalation is taking place. In this case the monitored pressure is likely to be relatively high, thus causing the actuator means to maintain the valve means in the closed condition.
2) The valve means is closed and inhalation is taking place. In this case the monitored pressure is relatively low, and probably slightly negative with respect to atmospheric, and this causes the actuator means to open the valve means for the preset period.
3) The valve means is open and exhalation is taking place. This condition is possible only when the delay means is maintaining the valve means open for the preset period and, during the period, the patient has switched from inhalation to exhalation. Once the valve means closes at the end of the preset period, the condition will revert to (1) above and will remain so until inhalation recommences.
4) The valve means is open and inhalation is taking place. In this case the monitored pressure is relatively high due to the pressure of oxygen being supplied to the patient but, despite this, the valve remains in the open condition for the remainder of the preset period.

It will be seen from the above that it is important with the "single tube" arrangement that the supply of oxygen is shut off at regular intervals during inhalation in order to allow the monitoring means to check for continued inhalation. During supply of oxygen to the patient the small negative pressure of inhalation is swamped by the pressure of the oxygen itself and it is not until the supply is halted that the monitor means is able to properly detect whether the patient is inhaling or exhaling.

Preferably said valve means comprises a movable member movable between a first position in which the valve means is closed and a second position in which the valve means is open and wherein said actuator means is operable upon sensing inhalation, to move said movable member from said first position to said second position and wherein said delay means is operable to cause said movable member to move back from said second position to said first position over a period equal to said pre-set period.

The movable member can take a number of forms, for example, a diaphragm or a piston. In a preferred embodiment of the invention, the movable member takes the form of a piston which is movable within a cylinder and is subject to balancing forces as between a biasing means, for example a spring on the one hand and pressure from said actuator means on the other. Preferably the pressure from the actuator means is gas pressure applied to the opposite side of said piston to the biasing means. Thus said actuator means comprises means for altering the gas pressure applied to said piston which results in movement of said piston, against the force of said biassing means, from said first position to said second position, or vice versa. For example, in one embodiment, the means for altering the gas pressure is operable to increase the gas pressure on said opposite side of the piston, thus moving the piston against the force of said biassing means, this movement being, in this case from the first (closed) position to the second (open) position. In another embodiment, the means for altering the gas pressure is operable to reduce the gas pressure on said opposite side of the piston, thus allowing the piston to move by the force of said biassing means, this movement being in this case from the first (closed) position to the second (open) position.

Preferably the means to alter the gas pressure comprises a further valve means operable to supply or withdraw gas pressure to or from said opposite side of said piston. Said valve means may be of any suitable type, for example a diaphragm valve or a piston-operated valve.

Thus, in one embodiment, means are provided for pressurising said opposite side of said piston, against the force of said biassing means, with sufficient pressure into said first position to normally maintain the first-mentioned valve means in the closed position, thereby cutting off the oxygen supply to the patient. A reduction in pressure at the outlet, indicative of inhalation, causes said further valve means to open which vents the opposite side of the piston, thus reducing the pressure and allowing the first-mentioned valve means to switch to the open position. This in turn results in an increased pressure at the outlet port, which increased pressure causes said further valve means to close again, thus cutting off the vent. Meanwhile, said pressurising means continues to supply gas to the opposite side of the piston so that, after a period governed by the speed at which the pressurising means is able to introduce gas to said opposite side of the piston, the first-mentioned valve means closes again, thus cutting off the supply to the patient, and the cycle repeats. This is explained in more detail hereinafter. Preferably the pressurising means incorporates a flow restrictor so as to increase this period. In practice, a period of about 0.5 seconds is typical.

In an alternative embodiment, the actuator means comprises two valves which act in tandem: A first valve acts to sense the pressure at the outlet port. A second valve is operable to switch the application of gas pressure to said opposite side of said piston. In this case, the first valve, which may for example be a diaphragm valve, actuates the second valve, which may for example be a piston-operated valve, to supply gas pressure to the opposite side of the piston of said first mentioned valve means, or not, as the case may be. The exact interrelationship of the first and second valves, and the first-mentioned valve means, is explained in more detail hereinafter.

A reservoir can be incorporated in the supply of gas to the first mentioned valve means in order to provide a pulse of increased pressure at the beginning of the inhalation period. The reservoir is preferably supplied via a flow restrictor, so that the reservoir and flow restrictor operate in tandem to enable the characteristics of the increased pressure at the beginning of inhalation to be tailored to requirements.

In order that the invention may be better understood, an embodiment thereof will now be described by way of example only and with reference to the accompanying drawings in which.

Figure 1:
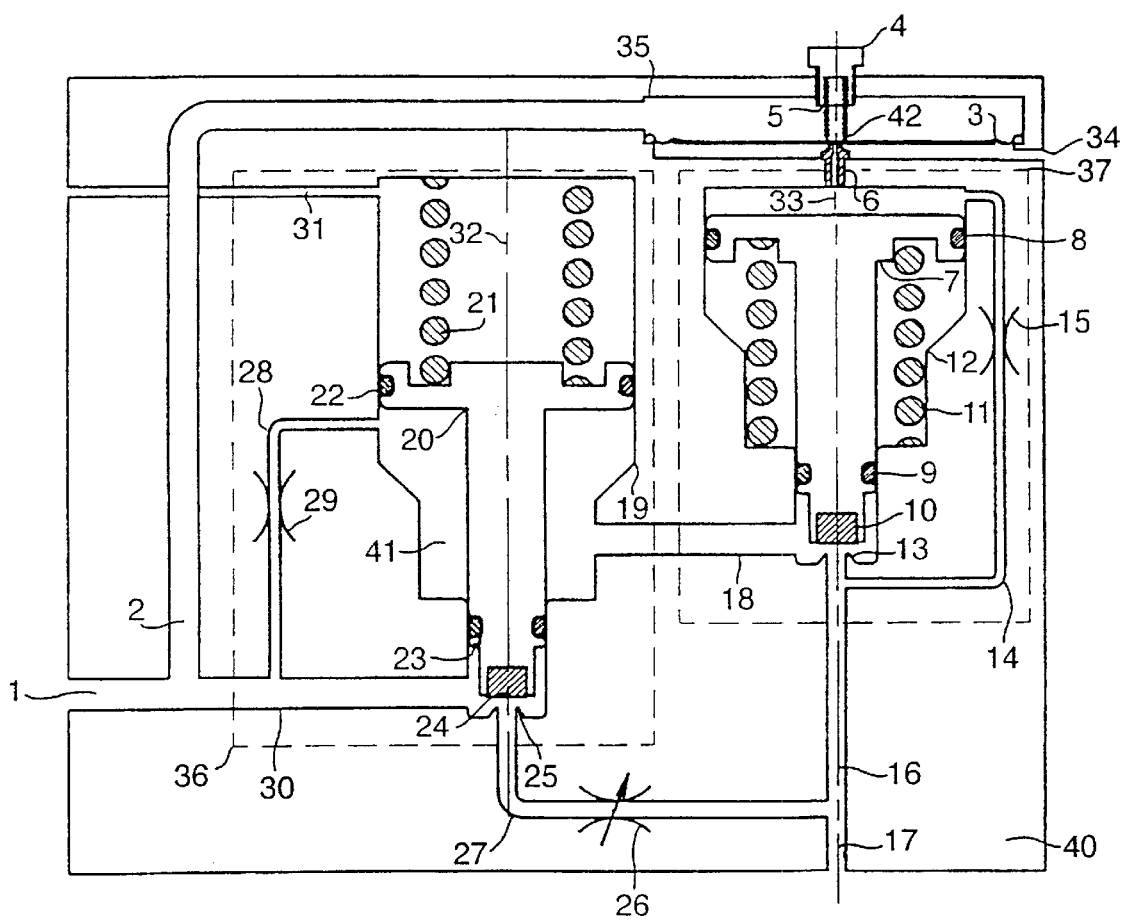
FIGS. 1 to 4 are sectional diagrams each illustrating one of four different embodiments of the invention.

Referring to FIG. 1, the oxygen economiser device comprises a block 40 in which are formed a number of passages which interconnect the three basic components of the device which are a diaphragm valve 42, a pressure actuated valve 36 and a pilot valve 37.

Oxygen is input to the device from an oxygen supply, for example an oxygen cylinder (not shown) at an inlet port 17 and is split along passages 16 and 27 to the pressure actuated valve 36 and pilot valve 37 respectively. The supply to the pressure actuated valve 36 is taken via a variable flow restrictor 26. A further passage 14 takes the input supply via a flow restrictor 15 to a chamber 33 and thence to the input of the diaphragm valve 42. The flow restrictor 15 may be made variable, for example, in the form of multiple selectable orifices.

The low pressure output to the patient is taken via a two-way outlet port 1 to a single tube cannula or single tube face mask (not shown).

The pilot valve 37 comprises a T-shaped inlet piston 7 which moves in a stepped bore 12 and is biased towards the top of the bore by a coil spring 11. The piston is sealed by "O" rings 8 and 9 with respect to the wider and narrower sections respectively of the bore 12. High pressure air enters the bottom of the bore 12, beneath the piston 7, via an inlet jet 13 and low pressure air exits from the bore 12 via a passage 18. A seat 10 of resilient material, such as nylon, is formed at the bottom end of piston 7 and acts to close off the jet 13, preventing or restricting flow therethrough, when the piston 7 is at or near its lowermost position.

The space above the piston 7 defines the aforementioned chamber 33 which has an output connection to an inlet jet 6 to the diaphragm valve 42. The diaphragm valve comprises a diaphragm 3 which passes across and normal seals the outlet to the jet 6. The diaphragm 3 extends across a diaphragm chamber 35 and divides the chamber into an upper pressurised part which is connected by passage 2 to port 1, and a lower unpressurised part which is vented to atmosphere at port 34. The force, and therefore the pressure needed to lift the diaphragm 3 from the outlet of jet 6, may be varied by means of a spring 5 and threaded hand wheel 4.

The pressure activated valve 36 comprises a T-shaped outlet piston 20 which moves in a stepped bore 19 and is biased towards the bottom of the bore by a coil spring 21. The piston is sealed by "O" rings 22 and 23 with respect to the wider and narrower sections respectively of the bore 19. High pressure air enters the bottom of the bore 19, beneath the piston 20, via an inlet jet 25 and low pressure air exits from below the piston 20 via a passage 30 to the port 1. A seat 24 of resilient material, such as nylon, is formed at the bottom end of the piston 20 and acts to close off the jet 25, preventing or restricting flow therethrough when the piston 20 is at or near its lowermost position.

The head of the piston 20 divides the bore 19 into an upper chamber 32 and a middle chamber 41. The upper chamber 33 is maintained at atmospheric pressure by means of a free-flow vent 31 and the middle chamber 41 is vented via a passage 28 and flow restrictor 29 to the passage 30.

The operation of the oxygen economiser device will now be explained in detail.

During inhalation, the patient draws oxygen from the outlet port 1 and through the single tube cannula or single tube face mask. During exhalation, the flow that the patient produces passes back down the single tube to the outlet port 1 and proceeds up the inlet passage 2 to the upper part of the diaphragm chamber 35. The output flow from the patient pressurises the diaphragm 3 and forces the diaphragm 3 onto the pilot jet 6. This effectively closes off the hole in the pilot jet 6 thus prohibiting flow from it. Due to the prohibition of flow through the pilot jet 6 the pressure within chamber 33 will increase thus forcing the inlet piston 7 down against the force of the coil spring 11. The chamber 33 is pressurised by a flow, restricted by flow restrictor 15, from the inlet port 17. The piston 7 is thus forced onto the inlet jet 13 and flow through this is prevented by the nylon seat 10. This means that there is zero flow through the passage 18 from the pilot valve 37 to the middle chamber 41 of the pressure actuated valve 36.

During the period that the patient is exhaling, the outlet piston 20 in the pressure actuated valve 36 is maintained in the lower position by the force of coil spring 21, thus sealing off the outlet jet 25 by means of the nylon seat 24. While the piston 20 is in this position it effectively seals off any flow to the outlet passage 30 and the middle chamber 41 is vented through the vent passage 28.

When the patient inhales through the single tube cannula or single tube face mask then a small negative pressure is formed within the diaphragm chamber 35, causing the diaphragm 3 to lift. The pressure required to lift the diaphragm 3 may be varied by turning the hand wheel 4. If the hand wheel 4 turned in a direction to thread it into the body, then the negative pressure required to lift the diaphragm 3 is increased. Due to the diaphragm 3 lifting, flow is now permitted to pass through the pilot jet 6 which in turn cause the pressure within the chamber 33 of the pilot valve 37 to fall. Any flow that passes through the pilot jet 6 is vented to atmosphere through the vent port 34. This fall in pressure in the chamber 33 allows the inlet piston 7 to rise, then breaking the seal between the inlet jet 13 and the nylon seat 10. This in turn allows the inlet flow from the inlet port 17 to flow through the passage 18 into the middle chamber 41 of the pressure actuated valve 36, thus causing a pressure increase within the chamber 41. This causes the outlet piston 20 to rise from the inlet jet 25 at the bottom of the piston 20 in the pressure actuated valve 36 thus permitting flow of the oxygen from the inlet port 17 through the passage 27 and flow restrictor 26 to the inlet jet 25. The flow restrictor allows an adjustable flow to the patient of from 0 to 15 liters/min through said outlet jet 25 and, via passage 30 and outlet port 1, to the patient through the single tube cannula or single tube face mask.

The rise in pressure in the passage 30 is sensed in the upper part of the diaphragm chamber 35 and causes the diaphragm once more to close off the jet 6. This in turn raises the pressure in chamber 33, causing piston 7 to lower and thus cut off the supply through jet 13 to passage 18 into the middle chamber 41 of the valve 36. The incoming supply of oxygen to the middle chamber 41 is thus terminated. Meanwhile, oxygen within the chamber 41 is continually leaking away, at a controlled rate, via the vent passage 28 and flow restrictor 29 to the passage 30. Once the incoming supply of oxygen is terminated, due to closure of the pilot valve 7 in the manner just described, this leakage starts to cause a continuous fall in the pressure within chamber 41 and consequently movement of the piston 20 in the downwards direction by the force of the coil spring 21. Eventually the flow through the inlet jet 25 is closed off, and flow from inlet port 17 to outlet port 1 ceases. The valve 36 thus effectively incorporates a time delay function which in practice is set to approximately 0.5 seconds, thus allowing oxygen to flow to the patient for this period. Upon closure of the pressure actuated valve 36 the pressure in passage 2 is sensed by the pilot valve 37 in the manner described above.

Figure 5:
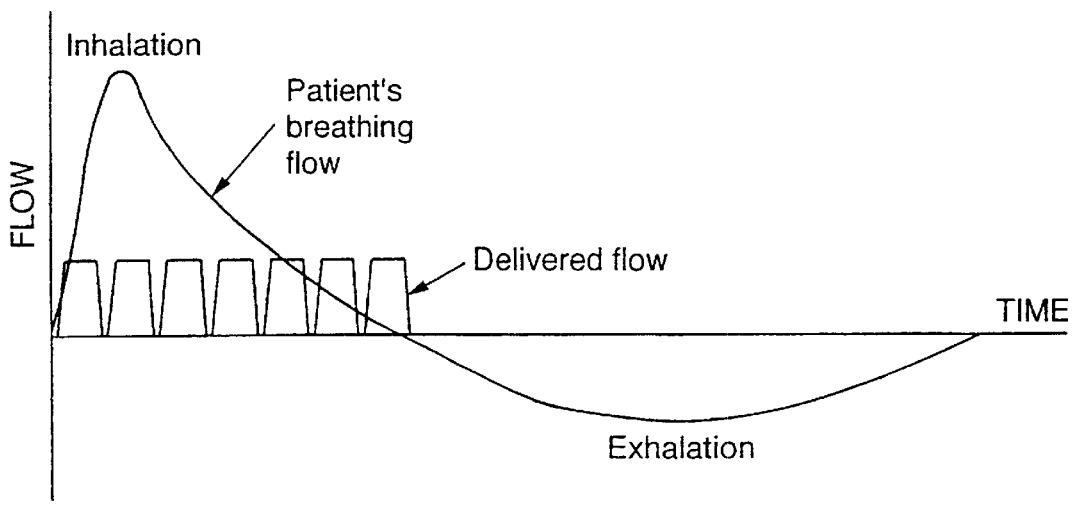
FIG. 5 is a graph of flow against time for the embodiments of FIGS. 1 and 2.

What happens next depends upon whether the patient is still inhaling, or has started to exhale. If the patient is still inhaling then the pressure in the upper part of chamber 35 will fall and the diaphragm 3 will be lifted again substantially instantaneously, allowing the flow to resume to the patient. If the patient is by now exhaling, then the diaphragm valve 42 will not be re-operated, causing the flow to the patient to cease. This means that during the period that the patient is inhaling there is a series of pulses of oxygen flow to the patient. This is clearly illustrated in FIG. 5. This action closely matches the effect of conventional (double tube) oxygen therapy whilst remaining compatible with current single tube cannulas and single tube face masks.

Figure 2:
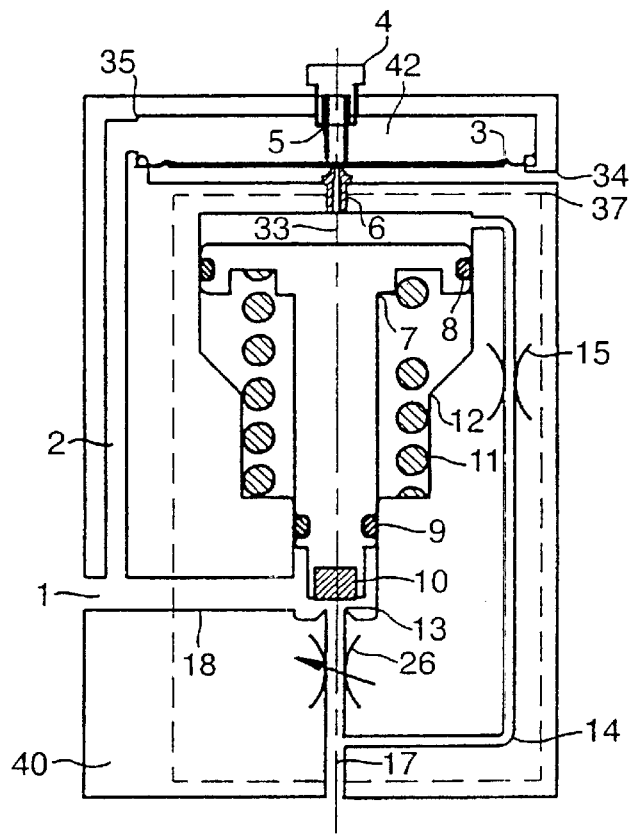

Referring now to FIG. 2 there is shown a second embodiment of the invention. The same reference numerals have been used again where appropriate.

The oxygen economiser device illustrated in FIG. 2 comprises a diaphragm valve 42 and a pilot valve 37, both constructed substantially as described above with reference to FIG. 1, so further explanation is omitted. The variable flow restrictor is placed in the input passage leading from the inlet orifice 17 to the jet 13. The passage 18 taking the output of the pilot valve is passed directly to the two-way outlet port 1 and the passage 2, communicating with the upper part of the diaphragm chamber 35, leads off it.

The operation will be apparent from the description given above of FIG. 1, the main difference being that the 0.5 second delay is achieved by the flow restrictor 15 controlling the time taken for the chamber 33 to be re-pressurised.

Briefly, on exhalation, the positive pressure sensed in the upper part of chamber 35 ensures that the nozzle 6 remains shut off, and the pressure in chamber 33 is relatively high, being supplied from the inlet port 17 via the passage 14 and flow restrictor 15. As a result, the piston 7 is forced down, and the resilient seat 10 closes off the jet 13, thus shutting off the supply to the patient.

Upon inhalation, the lowered pressure in the upper part of chamber 35 causes the jet 6 to be uncovered, and the chamber 33 is vented to atmosphere, thus lowering the pressure in the chamber and causing the piston 7 to be raised, thus opening the pilot valve and allowing oxygen to pass from the inlet port 17 to the outlet port 1 at a rate controlled, as described above, by the variable flow restrictor 26.

The resultant rise in pressure in the passage 18 is sensed in the upper part of the chamber 35 and the diaphragm valve 42 thus closes. Once this occurs, the pressure in chamber 33 starts to rise, supplied from the inlet port 17 via the passage 14 and flow restrictor 15. As the pressure in the chamber 33 rises, the piston 7 lowers and eventually the resilient seat 10 closes off the jet 13, thus cutting off the flow approximately 0.5 seconds after it started.

What happens next depends upon whether the patient is still inhaling, or has started to exhale. If the patent is still inhaling, then the diaphragm valve 42 opens again, thus re-starting the flow through the pilot valve 37 for a further 0.5 seconds. If the patient is by now exhaling, then the diaphragm valve remains shut until the next inhalation. The flow graph shown in FIG. 5 applies.

The embodiments of FIGS. 1 and 2 achieve essentially the same object but the FIG. 2 embodiment uses fewer components. The FIG. 1 embodiment has the advantage that the valve 37 only has to supply a pilot flow to the diaphragm valve 42 so its piston can be made smaller and the volume of chamber 33 made smaller, thus reducing the time the diaphragm has to be open in order to switch.

Figure 6:
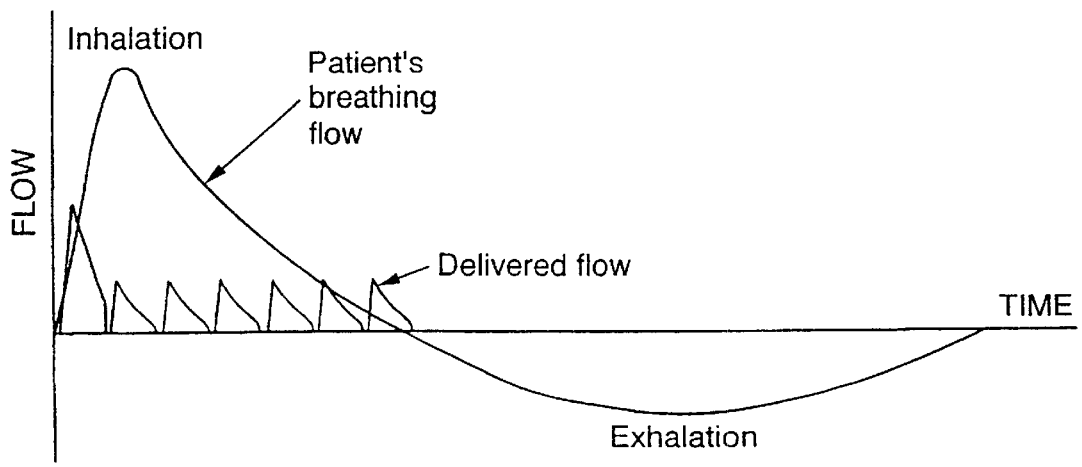
FIG. 6 is a graph similar to FIG. 5, but in respect of the embodiments of FIGS. 3 and 4.

As mentioned above, there can be benefits in supplying a higher rate of flow at the beginning of the inhalation cycle, this being illustrated graphically in FIG. 6. The embodiments of FIGS. 3 and 4, approximately equivalent to FIGS. 1 and 2 respectively, are intended to achieve this. Once again, like reference numerals have been used where appropriate, and the following description highlights just the differences.

Figure 3:
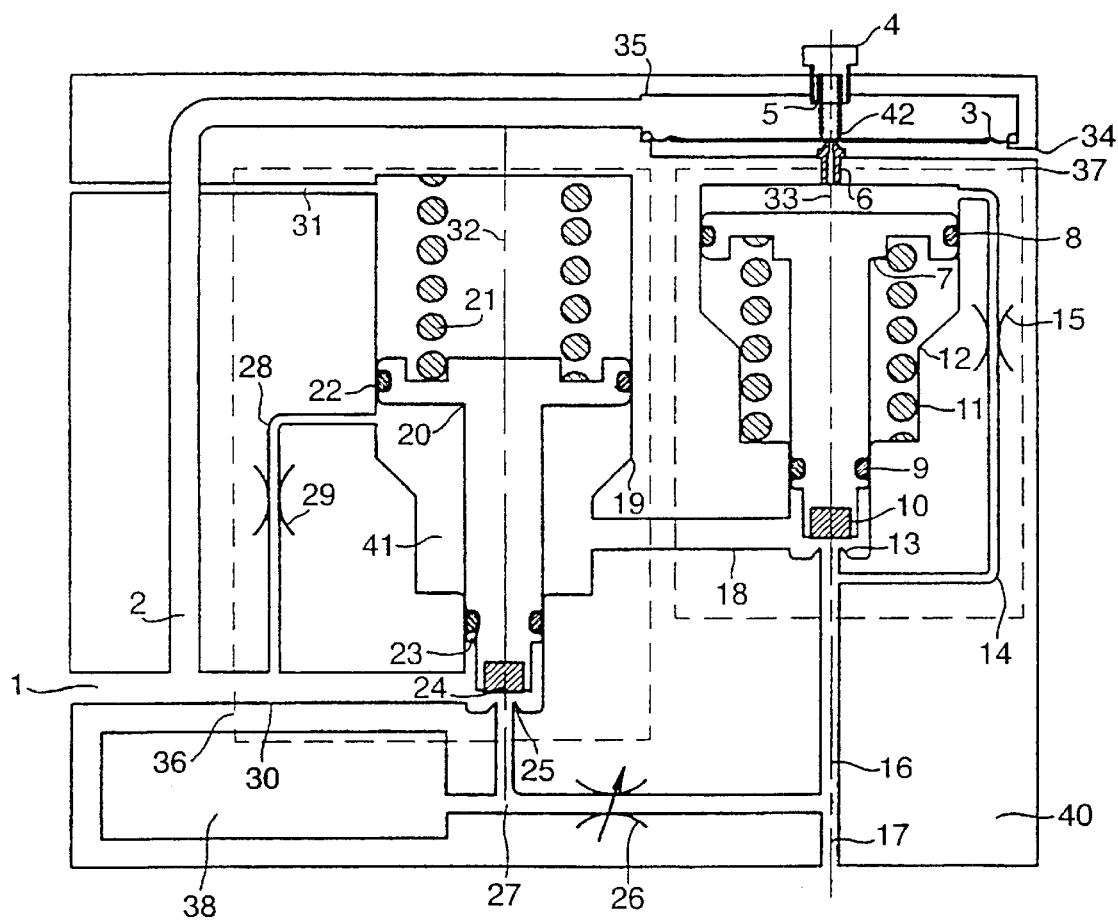

In the FIG. 3 embodiment, the device of FIG. 1 is modified by the addition of a reservoir 38 in the input to the pressure actuated valve 36. The connection between the reservoir 38 and the inlet port 17 is not via any valves so the reservoir is free to fill up during the whole of the inhalation/exhalation cycle. However, because the exhalation period is much longer than the individual (0.5 second) inhalation periods, the reservoir is able to fill up more during exhalation than during the brief inhalation periods. When the valve 36 opens, oxygen is supplied to jet 25 both from the inlet orifice 17 and from the reservoir 38. However, the supply is taken preferentially from the reservoir while the reservoir pressure is the higher of the two and therefore by carefully balancing the capacity of the reservoir 38 with the resistance to flow generated by the variable flow restrictor 26, a delivered flow similar to that shown in FIG. 6 can be achieved.

Figure 4:
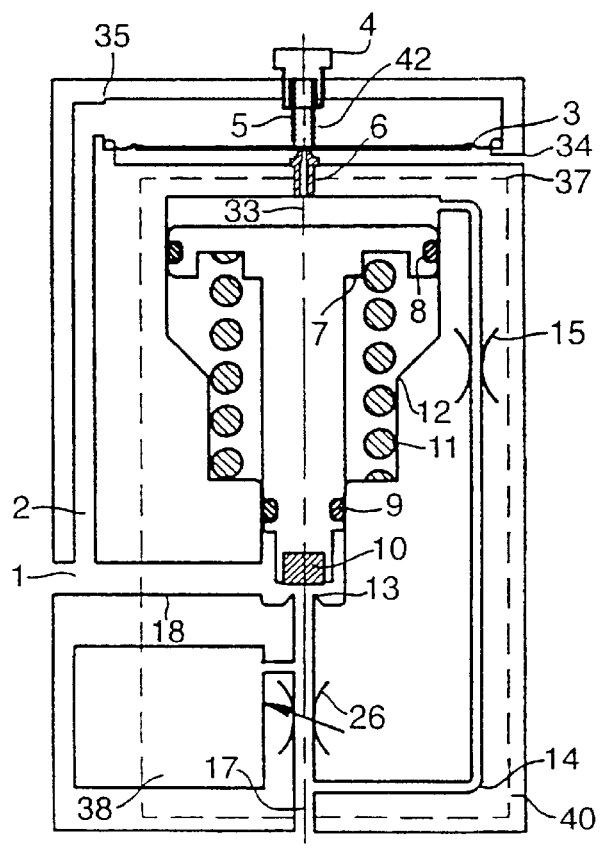

In the embodiment of FIG. 4, the reservoir 38 is connected between the variable flow restrictor 26 and the jet 13. Its operation, in conjunction with the flow restrictor 26 will be apparent without further explanation.

In alternative embodiments to FIGS. 3 and 4, the output of the reservoir 38 is taken to a second jet (not shown), separate from the jet 25 of FIG. 3 or the jet 13 of FIG. 4 but which is positioned so as to be sealed by the respective seat 24 or 10. The reservoir supply thus becomes separate from the supply from the inlet port 17 and this would enable a combination of characteristics to achieve a desired breathing trace.

The jet assemblies 10/13 and 24/25 do not have to be of the form shown; for example each assembly may take the form of a hole with a tapered pin seated in it to selectably seal the hole.

What is claimed is:

1. A pneumatically operated economiser device for supply of breathable gas to a patient, said device having an inlet port for receiving a supply of pressurised gas and an outlet port for delivering a supply of pressurised gas to the patient, valve means connecting the inlet port to the outlet port, means for monitoring whether the patient is inhaling or exhaling, said monitoring means having an inlet passage connected to said outlet port whereby the pressure of gas at said outlet port may be monitored, actuator means for causing the valve means to open so as to supply breathable gas to the patient in the event that the patient is inhaling, and delay means for causing the valve means to close after a preset period, thereby shutting off the supply of gas to the patient for a monitoring period so as to allow the monitoring means to check for continued inhalation and wherein in the event that the patient is still inhaling, the actuator means causes the valve means to open to re-establish the supply of gas to the patient.

2. A device as claimed in claim 1 in the event that the patient is exhaling during said monitoring period said actuator means causes the valve means to remain in the closed condition.

3. A device as claimed in claim 1 wherein said valve means is switchable between a first position in which flow of gas from the inlet port to the outlet port is shut off, and a second position in which gas may flow from said inlet port to said outlet port, and wherein said actuator means switches the valve means from said first position to said second position when the monitoring means detects inhalation by the patient.

4. A device as claimed in claim 3 wherein said monitoring means is such that, when the pressure at the outlet port during said monitoring period falls below a preset level, this is taken as indicative of inhalation by the patient.

5. A device as claimed in claim 4 wherein the actuator means is operable to switch the valve means to said first position at the end of the monitoring period; wherein, after the preset period, the monitoring means monitors the pressure at the outlet port, and wherein the actuator means is operable to switch the valve means back to said second position should the pressure at the outlet port, as detected by said monitoring means, be below said preset level indicative of inhalation, and wherein said delay means once again maintains the valve means in said second position for said preset period.

6. A device as claimed in claim 5 wherein the preset period is sufficiently small as to enable multiple switching cycles of said valve means between said first and second positions during inhalation, resulting in a pulsed flow of breathable gas to the patient.

7. A device as claimed in claim 5 wherein the actuator means is operable to maintain the valve means in said first position should the pressure at the outlet port, as detected by said monitoring means during said monitoring period, be above said preset level, indicative of exhalation.

8. A device as claimed in any claim 3 wherein said valve means comprises a movable member movable between a first position in which the valve means is closed and a second position in which the valve means is open and wherein said actuator means is operable, upon sensing inhalation, to move said movable member from said first position to said second position and wherein said delay means is operable to cause said movable member to move back from said second position to said first position over a period equal to said pre-set period.

9. A device as claimed in claim 8 further comprising means for supplying gas pressure to said movable member, and wherein said actuator means comprises means for altering the gas pressure applied to said movable member which results in movement of said movable member from said first position towards said second position or vice versa.

10. A device as claimed in claim 9 wherein the means to alter the gas pressure comprises a further valve means operable, upon a reduction in pressure at the outlet port to below said preset level, to cause the gas pressure applied to said movable member to be vented, thus resulting in movement of said movable member from said closed position towards said open position.

11. A device as claimed in claim 9 wherein said means for supplying gas pressure to said movable member includes a flow restrictor whereby the rate of supply of gas can be reduced to provide for said preset period.

12. A device as claimed in claim 9 wherein the means to alter the gas pressure comprises two valves which act in tandem, namely a first valve which acts to sense the pressure at the outlet port and a second valve which is operable to control the application of gas pressure to the movable member.

13. A device as claimed in claim 12 wherein vent means are provided to vent the gas pressure applied to said movable member, said vent means incorporating a flow restrictor to limit the rate of venting to provide for said preset period.

14. A device as claimed in claim 1 further comprising a reservoir connected to the inlet port.

15. A device as claimed in claim 14 in which a flow restrictor is placed in the connection to the reservoir.

16. A pneumatically operated economiser device for supply of breathable gas to a patient, said device comprising an inlet port for receiving a supply of pressurised gas and an outlet port for delivering pressurised gas to the patient;

a selectively controllable flow valve system connecting the inlet port to the outlet port operable to provide breathable gas from said inlet port to said outlet port in pulses such that a monitoring interval is defined between pulses when said valve system operates to provide breathable gas from said inlet port to said outlet port;

a monitoring system in direct communication with said outlet port for sensing inhalation and exhalation of a patient when a pulse of gas is not being provided to said outlet port; and said monitoring system operatively associated to control said flow valve system when a pulse of gas is not being provided to said outlet port such that, when inhalation is sensed at said output port, said flow valve system is permitted to operate and, when exhalation is sensed at said output port, said flow valve system is shut off.

17. A device as claimed in claim 16 wherein said selectively controllable flow valve system includes a pneumatically controlled breathable gas flow valve connecting said inlet port to said outlet port operable and a pneumatic control for said flow valve having at least one flow restrictor for defining a pulse flow of gas through said flow valve when said selectively controllable flow valve system is operated to provide breathable gas from said inlet port to said outlet port.

18. A device as claimed in claim 17 wherein said monitoring system includes a pneumatically controlled diaphragm valve having a control passage in direct communication with said outlet port, said diaphragm valve operatively connected to said flow valve system to permit and shut off operation thereof.

19. A device as claimed in claim 18 wherein said pneumatic control for said flow valve includes a pilot valve.

20. A device as claimed in claim 18 further comprising a reservoir of breathable gas connected to said inlet port.

* * * * *